United States Patent
Schiff et al.

(10) Patent No.: US 6,381,026 B1
(45) Date of Patent: Apr. 30, 2002

(54) METHOD OF MEASURING THE CONTOUR OF A BIOLOGICAL SURFACE

(75) Inventors: Charles M. Schiff, The Woodlands; Greg Abott, Houston, both of TX (US)

(73) Assignee: LifeCell Corp., Branchburg, NJ (US)

( * ) Notice: Subject to any disclaimer, the term of this patent is extended or adjusted under 35 U.S.C. 154(b) by 0 days.

(21) Appl. No.: 09/268,266

(22) Filed: Mar. 15, 1999

(51) Int. Cl.[7] .............................................. G01B 11/24
(52) U.S. Cl. ...................................................... 356/601
(58) Field of Search ................................. 356/601, 614, 356/602–613

(56) References Cited

U.S. PATENT DOCUMENTS

| | | | |
|---|---|---|---|
| 3,735,036 A | 5/1973 | Macovski | 178/6.8 |
| 3,828,126 A | 8/1974 | Ramsey, Jr. | 178/6.8 |
| 3,986,774 A | 10/1976 | Lowrey, Jr. et al. | 356/3 |
| 4,091,274 A | 5/1978 | Angelbeck et al. | 250/201 |
| 4,212,073 A | 7/1980 | Balasubramanian | 364/562 |
| 4,375,921 A | 3/1983 | Morander | 356/381 |
| 4,548,504 A | 10/1985 | Morander | 356/375 |
| 4,563,095 A | 1/1986 | Puffer | 356/430 |
| 4,645,337 A | 2/1987 | Obenreder | 356/128 |
| 4,911,511 A | 3/1990 | Morander | 356/376 |
| 5,055,664 A | 10/1991 | Ryczek | 250/201.4 |
| 5,446,549 A | 8/1995 | Mazumder et al. | 356/376 |
| 5,714,762 A | 2/1998 | Li et al. | 250/559 |
| 5,967,979 A | * 10/1999 | Taylor et al. | 356/614 |

OTHER PUBLICATIONS

Article entitled "Laser Based Precision Measurements," *PreciMeter AB*, No date available.
Leaflet and flyer describing "DMEyes Description," *Vision Metrics, Inc.*, pp. 1–4, No date available.
Article entitled "Noncontact Device Measures Wounds With Light," *Biophotonic International*, Mar./Apr. 1998, No date available.
Article entitled "Precimeter II," *Measurement Technologies, Inc.*, No date available.

* cited by examiner

Primary Examiner—Frank G. Font
Assistant Examiner—Amanda Merlino
(74) Attorney, Agent, or Firm—Howrey Simon Arnold & White LLP; Stephen H. Cagle; Carter J. White

(57) ABSTRACT

A method of determining the dimensional characteristics of a biological object included: measuring without physical contact or disruption of sterility the length, width and height above or below a reference plane of the biological object with an optical distance measuring device thereby creating a data set; and processing the data set in a computer so as to determine the dimensional characteristics of the biological feature. Preferably the optical distance measuring means is a laser based distance measuring device and the storage of x axis values, y axis values and distance values is in the electronic memory of a computer. The biological surface may be a wound bed or a dermal surface, or alternatively the biological surface may be vascular tissue including heart valves, veins and arteries.

18 Claims, 3 Drawing Sheets

METHOD OF MEASURING THE CONTOUR OF A BIOLOGICAL SURFACE

BACKGROUND

There exists a need in the medical arena to know the surface contour of a feature on a living subject without coming into contact with the subject. Determining, the contour of a biological surface is especially important in situations in which contacting the surface to be measured is not desired. In particular, contact with the biological surface may not be desired due to, the measuring means changing the contour of the surface, the contour changes are small or difficult to measure consistently, contact with the surface may results in the transmission of bacteria or other infectious agents.

An example of this need occurs during the replacement of heart valves or other vascular grafts. During such transplants it is important that the diameter and size of the transplant tissue be approximately that of the vascular tissue in the recipient site. Typically these measurements are conducted during surgery by comparing the diameter of the recipient's vascular tissue with a size chart. A precision caliper can not be used in such situations because of the difficulty in sterilizing the measuring device. As a result, the attending surgeon can only make an approximation as to the diameter of vascular tissue at the graft site. In a similar manner the proper measurement of the vascular tissue at the donor site is difficult because of the pliable nature of the tissue. Although in many cases an estimated measurement of the recipient site tissue and the donor tissue is suitable, a more precise fit could lead to better and more rapid healing.

SUMMARY OF THE INVENTION

The present invention provides for a method of making contour measurements in a precise manner without contacting or otherwise disturbing the biological surface of the tissue. Generally the method involves the measuring the contour of a biological surface without physically contacting the biological surface. Such a method includes defining a reference plane relative to the biological surface. The reference plane is defined by the x axis and y axis of a mechanized x-y positional axis means coupled to an optical distance measuring means. A first distance from the reference plane to the biological surface is measured using the optical distance measuring means and a value of the first x axis position and a value of the first y axis position of the optical distance measuring means in the reference plane and the first distance are stored in a register of x axis position, y axis position and distance. The optical measuring means is then moved a predetermined distance along the x-axis, the y axis or both to a second position and a second distance from the reference plane to the biological surface is measured using the optical distance measuring means. The values of the second x axis position, the second y axis position and the second distance are stored in a register of x axis position, y axis position and distance. A relative height value may be then calculated by subtracting the first distance from the second distance. A plotting the x axis position, y axis position and relative height value on an orthographic x, y, z coordinate system results in a three dimensional plot of values that is representative of the contour of the biological surface.

The above described method may also include moving the optical measuring means to a series of predetermined positions in the reference plane; measuring the distance from each predetermined position to the biological surface using the optical distance measuring device; storing the x axis position value, the y axis position value and the distance for each predetermined position in the reference plane in a register of x axis position values, y axis position values and distance values; and subtracting the first distance from the distance for each predetermined position to give a relative height value. The values of x axis position, y axis position, and relative distance may be stored in the electronic memory of a computer thereby generating a data set of values which may be mathematically manipulated. In one preferred embodiment, the optical distance measuring means is a laser based distance measuring device. The biological surface may be a wound bed or a dermal surface. or it may be vascular tissue including heart valves, veins and arteries.

These and other features of the present invention are more fully set forth in the following description of illustrative embodiments of the invention.

BRIEF DESCRIPTION OF THE DRAWINGS

The following description is presented with reference to the accompanying drawings in which.

DESCRIPTION OF ILLUSTRATIVE EMBODIMENTS

The present invention is generally directed to a method involving the measuring the contour of a biological surface without physically contacting the biological surface.

The method of the present invention may be carried out using a wide variety of apparatus and still be within the contemplation of the present invention. One such exemplary apparatus as described below and generally shown in FIG. 1.

Figure 1:
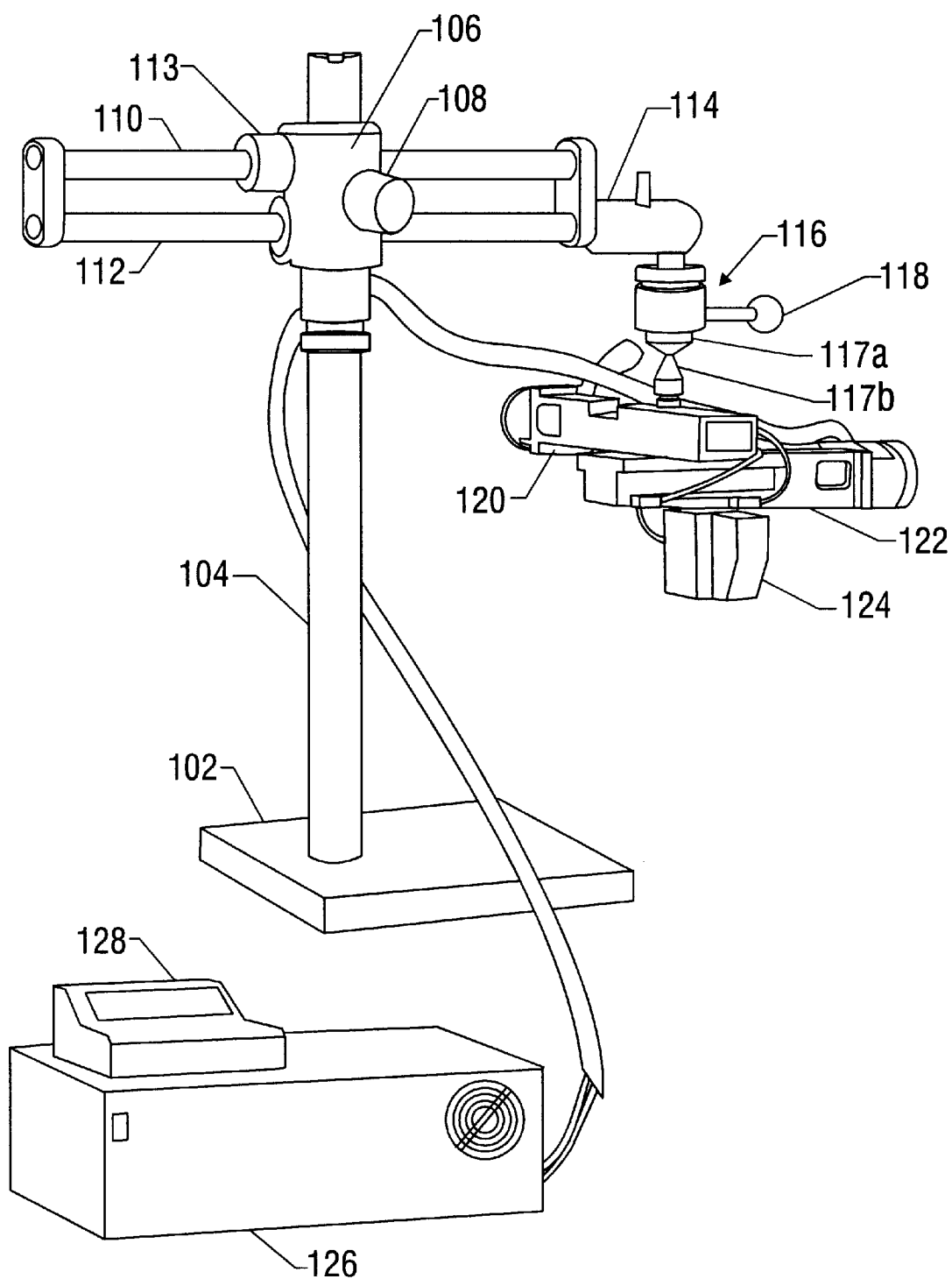
FIG. 1 is an illustration of an apparatus useful in practicing the method of the present invention.

With reference to FIG. 1, the exemplary apparatus includes a support and stabilizing means such as a movable support base 102 and support upright 104. The support upright is functionally connected by way of a vertical position control fixture 106 to a horizontal positioning means such as the upper and lower horizontal support arms 110 and 112 respectively. The vertical position of the vertical position control fixture is by the manual adjustment of the vertical control knob 108 although this may be done by mechanical means with a suitable motorized system. The support upright may be permanently fixed in place, thus eliminating the need for support base 102. Alternatively, the support base and support upright may be replaced by a vertical track set into or affixed to a wall in which case a motorized system of adjusting the vertical position may be desirable. This latter embodiment could be used in a clinical setting such as in an operating room or other treatment room where space and location of equipment is important. In yet another alternative, the support upright can be fixed to a cart or a similar such sturdy but mobile base to aid in the mobility of the apparatus.

The horizontal position of the horizontal support arms is controlled by the horizontal position control knob 113 on the upper horizontal support arm. Although two horizontal support arms are shown, the elimination of one or the addition of a third or fourth arm is within the contemplation of the present invention. On one end of the upper and lower horizontal support arms is a horizontal support arm mounting fixture 114 which allows for the mounting of ball joint 116 which includes a ball joint socket 117A and a ball joint ball 117B. The ball joint allows for additional positional degrees of freedom for the apparatus. As shown the ball joint socket 117A is fixedly mounted to the horizontal support arm mounting fixture. The ball joint is controlled by the ball joint control arm 118. Attached to the ball joint ball 117B is a motor driven x-axis 120 and a motor driven y-axis 122. Each of the motor driven axis are of a conventional rack and pinion type however, screw type and other similar x-axis, y-axis mechanisms may be used. As shown, the motor driven x-axis is rigidly fixed to the ball of the ball joint and movably fixed to the motor driven y-axis so that activation of the motor in the motor driven x-axis causes the motor driven y-axis to move back and forth along the x-axis. Movably mounted to the motor driven y-axis is a laser-based distance measuring means. Activation of the motor in the motor driven y-axis causes the laser-based distance measuring means to move back and forth along the y-axis. Thus one of ordinary skill should understand and appreciate that the above combination of motor driven x-axis and motor driven y-axis allows for the positioning of the laser-based distance measuring mean to any point within the plane defined by the motor driven x-axis and the motor driven y-axis. The purpose for the laser-based distance measuring means is to accurately measure the relative distance from the x–y plane defined by the motor driven x-axis and motor driven y-axis as described above. In one preferred embodiment the laser-based distance measuring means is a Percimeter II Displacement measuring system available from Measurement Technologies, Inc. The laser-based distance measuring means should be capable of measuring distances within a range of about +/−20 cm with a resolution greater than $1\times10^{-5}$ m.

The motors of the motor driven x-axis and the motor driven y-axis are in electrical communication via a control and data cable bundle 130 to a programmable control box 126. The laser based distance measuring device is likewise in electrical communication via the control and data cable bundle 130 with a programmable control box for the laser measuring means 128. The position information of the motor driven x-axis and the motor driven y-axis and the distance information from the laser-based distance measuring means may be transferred electronically from the respective programmable control boxes to a personal computer (not shown). Once the data is present in the personal computer, the data can be processed so that a plot of x-axis position, y-axis position and distance can be made. Alternatively, a plotter capable of drawing in three dimensions may be used to give an image of the distance data in relation to the x-axis and y-axis.

Figure 2:
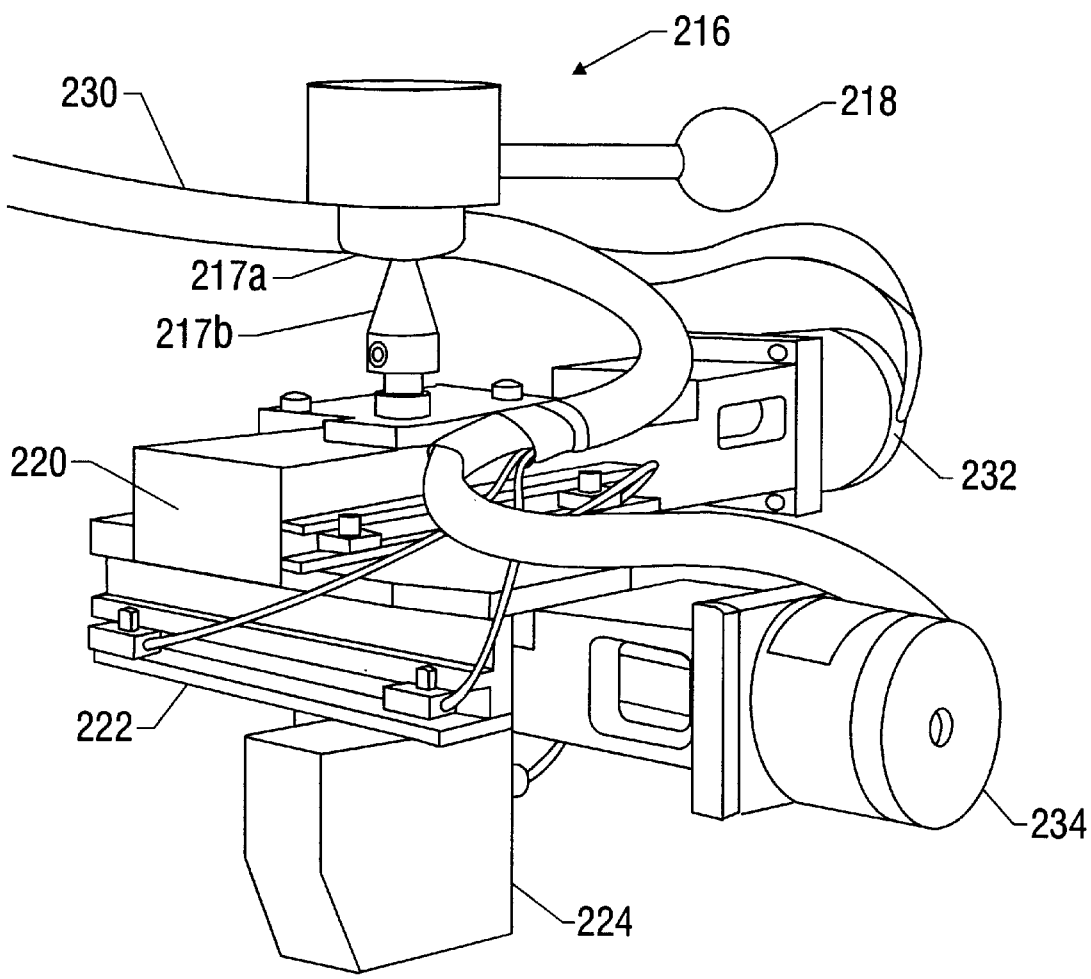
FIG. 2 is an detailed illustration of the motorized x-axis, y-axis of the apparatus in FIG. 1.

A closer view of the arrangement of the motor driven x-axis, the motor driven y-axis and the laser-based distance measuring means is shown in FIG. 2. It should be noted that the figure reference numbers for items previously shown and described in FIG. 1 have retained the same last two digits of the reference number and that the first digit has been increased by one in FIG. 2. For example the laser based distance measuring means in FIG. 1 has a reference number of 124 while the same structure in FIG. 2 has a reference number of 224. Returning to FIG. 2, ball joint 216 includes a control arm 218, which controls the motion of the ball joint. The socket 217A of the ball joint is rigidly fixed to horizontal support arm mounting fixture (not shown) and within the socket is a movable ball 217B. The ball portion of the ball joint is rigidly attached to a motor driven x-axis 220 which in turn is functionally connected to a motor driven y-axis 222 as previously described. The motor for the motor driven x-axis 232 and the motor for the motor driven y-axis 234 are shown. Control and data cable bundle 230 is shown with control, power and data cables extending and functionally being attached to the motor driven x-axis, the motor driven y-axis and the laser based distance measuring means 224.

The above described apparatus has been presented as an illustration of one of a variety of possible apparatus that may be used to carry out the method of the present invention. One of skill in the art should be able to design and build an apparatus of a similar nature that provides the following characteristics: the apparatus defines a reference plane having an orthogonal coordinate system, a means for measuring the relative distance from the reference plane to the surface contour to be measured, means for controlling the position of the means for measuring the relative distance from the reference plane to the surface contour being measured, and means for gathering data on the position within the reference plane of the measurement means and the value of the relative distance.

Figure 3:
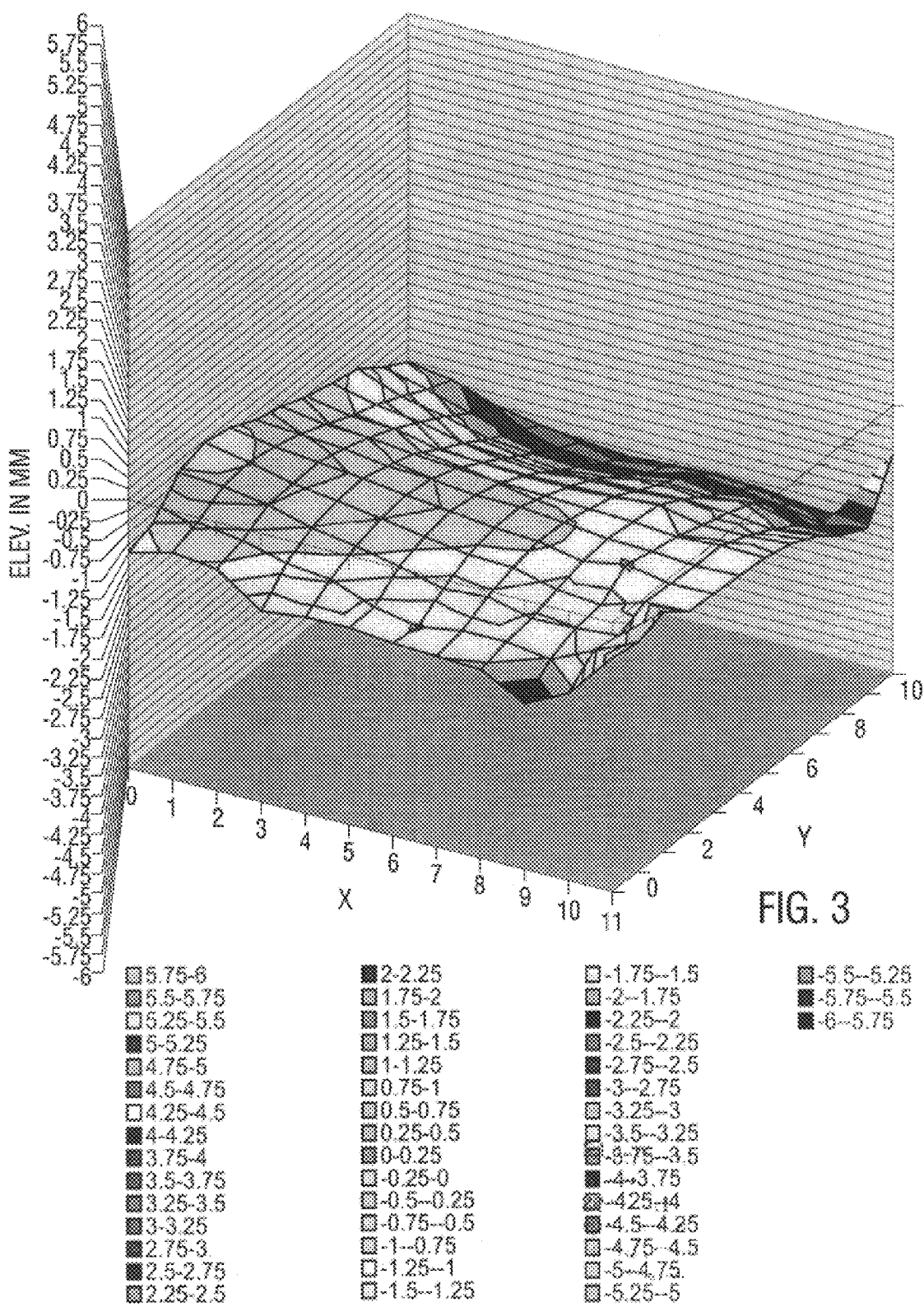
FIG. 3 is a plot of data resulting from the practice of the method of the present invention measuring the relative height of the contour of a biological sample

Turning now to the method of the present invention, as previously noted the methods of the present invention is generally directed to a method of making contour measurements of a biological surface without physically contacting the biological surface. Such a method includes defining a reference plane relative to the biological surface. The reference plane is defined by the x axis and y axis of a mechanized x–y positional axis means coupled to an optical distance measuring means, such as that shown in FIG. 1 and 2 and described above. In one preferred embodiment, the optical distance measuring means is a laser based distance measuring device. A first distance value from the reference plane to the biological surface is measured using the optical distance measuring means. The value of the first x axis position and a value of the first y axis position of the optical distance measuring means in the reference plane and the first distance value are recorded as the first entry in a register of x axis position, y axis position and distance values. Preferably, the register is an electronic register such as that provided by a computer. The optical measuring means is then moved a predetermined distance along the x-axis, the y axis or both to a second position. A second distance from the reference plane to the biological surface is measured using the optical distance measuring means and the values of the second x axis position, the second y axis position and the second distance are stored as a second entry in the register of x axis position, y axis position and distance. A relative height value may be calculated by subtracting the first distance from the second distance. A plotting the x axis position, y axis position and relative height value on an orthographic x, y, z coordinate system results in a three dimensional plot of values that is representative of the actual contour of the biological surface. An example of such a plot is shown in FIG. 3 in which the contour of a biological sample, in this case the surface contour of a portion of a pig's back, is shown.

The above described method may also include moving the optical measuring means through a series of predetermined positions in the reference plane and measuring the distance from each predetermined position to the biological surface using the optical distance measuring device. In this way the process of scanning any particular surface may be made more efficient and more consistent. Alternatively, the predetermined positions can be selected so that the most important data points are measured first and then less important data points measured as time permits. One of skill in the art should appreciate that such variation in the method of the present invention may be made without departing from it's scope. In any case, the x axis position, the y axis position and the distance for each predetermined position in the reference plane are stored in a register of x axis values, y axis values and distance values. By subtracting the value of a predetermined reference distance from the distance for each predetermined position a relative height value can be determined. The values of x axis position, y axis position, and the relative distance may be stored in the electronic memory of a computer thereby generating a data set of values which may be mathematically manipulated as desired. For example, values may be weighted or multiplied by a fixed value in order to enhance the visualization of small relative height values. Alternatively, the data may be plotted without processing on a suitable three dimensional plotter which produces images of the data like that in FIG. 3.

An alternative embodiment of the present invention may also included a means for aiding in the aligning the relative plane with that of the surface to be scanned. Such a means may included a means for projecting the silhouette or image of a predetermined shape, such as a circle, square, triangle, rectangle, etc. . . onto the surface to be scanned. Such a projector may included a light source, a reticule through which the light from the light source passes and forms the desired image and a focusing lens for the image. The projector may be mounted along side the laser based distance measuring means an the x-axis/y-axis. Alternatively a fiber optic cable may be used in combination with a reticule and a focusing lens, the reticule and focusing lens being mounted on a portion of the laser based distance measuring means. IN either case, the focusing lens should be optically aligned to project the image generated by the passage of light through the reticule onto the surface to be scanned. In the latter case in which a fiber optic cable is used, the fiber optic cable would be part of the cable bundle and the light source would be located remotely but in optical communication with the fiber optic. The addition of the above described alignment device would aid in the positioning of the relative plane over the area of interest with the greatest possible accuracy in the least amount of time. Such an embodiment is especially useful in animal studies because of the lack of cooperation by the test animal in staying in a fixed position.

The biological surface may be a wound bed or a dermal surface. or it may be vascular tissue including heart valves, veins and arteries. One of ordinary skill in the art should appreciate that the method and apparatus of the present invention may have many uses. One such use might be in medical research to study the changes in a wound during the healing process by comparing scans of the wound at set time intervals. another use of the method of the present invention is the measurement of vascular conduits during surgery so that an accurate matching of the vascular tissue at the transplant recipient site and the vascular tissue at the donor site. Yet another use of the present invention may be to chart the growth or decline of human skin lesions, again by comparing scans of the same area. Such application could be very useful in determining if growths on or just below the surface of the skin are being affected by a specific treatment. Another such application could be in reconstructive surgery in which certain contours are desired and the monitoring of the reabsorption of implants is desired. Additional applications are numerous and include almost any situation where sterile, non-contact and accurate measurement of surface topography is required.

In view of the forgoing description, one of ordinary skill in the art should understand that the present invention encompasses an illustrative embodiment which includes a method of measuring the contour of a biological surface without physically contacting the biological surface. Such an illustrative method may include: defining a reference plane relative to the biological surface, the reference plane being defined by the x axis and y axis of a mechanized x-y positional axis means coupled to an optical distance measuring means; measuring a first distance from the reference plane to the biological surface using the optical distance measuring means; storing a value of the first x axis position and a value of the first y axis position of the optical distance measuring means in the reference plane and the first distance in a register of x axis position, y axis position and distance; moving the optical measuring means a predetermined distance along the x-axis, the y axis or both to a second position; measuring a second distance from the reference plane to the biological surface using the optical distance measuring means; storing a value of the second x axis position and a value of the second y axis position of the optical distance measuring means in the reference plane and the second distance in a register of x axis position, y axis position and distance; subtracting the first distance from the second distance to give a relative height value; and plotting the x axis position, y axis position and relative height value on an orthographic x, y, z coordinate system so as to give the contour of the biological surface. The illustrative method may further include: moving the optical measuring means to a series of predetermined positions in the reference plane; measuring the distance from the predetermined position to the biological surface using the optical distance measuring device; storing the x axis position, the y axis position and the distance for each predetermined position in the reference plane in a register of x axis values, y axis values and distance values; and subtracting the first distance from the distance for each predetermined position to give a relative height value. In one preferred embodiment the optical distance measuring means is a laser based distance measuring device. In order to maximize the ability to manipulate the data, the storage of x axis values, y axis values and distance values may be in the electronic memory of a computer. The method of the present invention may be carried out in such cases in which the biological surface may be a wound bed or a dermal surface or alternatively, the biological surface may include vascular tissue including heart valves, veins and arteries.

An alternative embodiment within the scope of the present invention includes a method of measuring the contour of a biological surface. An illustrative embodiment of such a method may include: defining a reference plane relative to the biological surface; measuring a first distance from a predetermined first position in the reference plane to the biological surface using the optical distance measuring means; storing the value of the predetermined first x axis position and the value of the predetermined first y axis position of the optical distance measuring means in the reference plane and the first distance in a register of x axis position, y axis position and distance; moving the optical measuring means to a series of predetermined x axis and y axis positions in the reference plane; measuring the distance from each of the predetermined positions in the reference plane to the biological surface using the optical distance measuring device; storing the predetermined x axis position, the predetermined y axis position and the distance for each predetermined position in the reference plane in a register of x axis position, y axis position and distance; subtracting the first distance from the distance for each predetermined position to give a relative height value and plotting the x axis position, y axis position and relative height value on an orthographic x, y, z coordinate system so as to give the contour of the biological surface. Preferably the reference plane is defined by the predetermined x axis position and the predetermined y axis position of a mechanized x-y positional axis means coupled to an optical distance measuring means. The method may include the included the use of a laser based distance measuring device as the optical distance measuring means. In one preferred embodiment of the illustrative method, the storage of x axis values, y axis values and distance values is in the electronic memory of a computer. This is especially useful when the weighting of the data to enhance the visualization of the contour is desired. The biological surface may be a wound bed or a dermal surface or alternatively the biological surface may be vascular tissue including heart valves, veins and arteries.

Yet another embodiment of the present invention includes a method of determining the dimensional characteristics of a biological object. Such and embodiment includes: measuring without physical contact or disruption of sterility the length, width and height above or below a reference plane of the biological object with an optical distance measuring device thereby creating a data set; and processing the data set in a computer so as to determine the dimensional characteristics of the biological feature. The optical distance measuring means is preferably a laser based distance measuring device which is capable of generating a data set is comprised of x axis values, y axis values and distance values relative to a predetermined reference plane. The data set may be stored in the electronic memory of a computer and then processed by the computer as time and computer work load allows. In one preferred embodiment the biological object is a wound bed or a dermal surface. Alternatively the biological object may be vascular tissue including heart valves, veins and arteries.

While the structures and methods of the present invention have been described in terms of preferred embodiments, it will be apparent to those of skill in the art that variations may be applied to the what has been described herein without departing from the concept and scope of the invention. All such similar substitutes and modifications apparent to those skilled in the art are deemed to be within the scope and concept of the invention as it is set out in the following claims.

What is claimed is:

1. A method of measuring the contour of a biological surface without physically contacting the biological surface, the method comprising:

defining a reference plane relative to the biological surface, the reference plane being defined by the x axis and y axis of a mechanized x-y positional axis means coupled to an optical distance measuring means;

measuring a first distance from the reference plane to the biological surface using the optical distance measuring means;

storing a value of the first x axis position and a value of the first y axis position of the optical distance measuring means in the reference plane and the first distance in a register of x axis position, y axis position and distance;

moving the optical measuring means a predetermined distance along the x-axis, the y axis or both to a second position;

measuring a second distance from the reference plane to the biological surface using the optical distance measuring means;

storing a value of the second x axis position and a value of the second y axis position of the optical distance measuring means in the reference plane and the second distance in a register of x axis position, y axis position and distance;

subtracting the first distance from the second distance to give a relative height value; and plotting the x axis position, y axis position and relative height value on an orthographic x, y, z coordinate system so as to give the contour of the biological surface.

2. The method of claim 1 further comprising:

moving the optical measuring means to a series of predetermined positions in the reference plane;

measuring the distance from the predetermined position to the biological surface using the optical distance measuring device;

storing the x axis position, the y axis position and the distance for each predetermined position in the reference plane in a register of x axis values, y axis values and distance values; and subtracting the first distance from the distance for each predetermined position to give a relative height value.

3. The method of claim 1 wherein the optical distance measuring means is a laser based distance measuring device.

4. The method of claim 1 wherein the storage of x axis values, y axis values and distance values is in the electronic memory of a computer.

5. The method of claim 1 wherein the biological surface is a wound bed or a dermal surface.

6. The method of claim 1, wherein the biological surface is vascular tissue including heart valves, veins and arteries.

7. The method of claim 1, wherein the relative height value has a uncertainty of less than 0.1 inches (0.25 cm).

8. A method of measuring the contour of a biological surface, the method comprising:

defining a reference plane relative to the biological surface, the reference plane being defined by the predetermined x axis position and the predetermined y axis position of a mechanized x-y positional axis means coupled to an optical distance measuring means;

measuring a first distance from a predetermined first position in the reference plane to the biological surface using the optical distance measuring means;

storing the value of the predetermined first x axis position and the value of the predetermined first y axis position of the optical distance measuring means in the reference plane and the first distance in a register of x axis position, y axis position and distance;

moving the optical measuring means to a series of predetermined x axis and y axis positions in the reference plane;

measuring the distance from each of the predetermined positions in the reference plane to the biological surface using the optical distance measuring device;

storing the predetermined x axis position, the predetermined y axis position and the distance for each predetermined position in the reference plane in a register of x axis position, y axis position and distance;

subtracting the first distance from the distance for each predetermined position to give a relative height value and plotting the x axis position, y axis position and relative height value on an orthographic x, y, z coordinate system so as to give the contour of the biological surface.

9. The method of claim 8 wherein the optical distance measuring means is a laser based distance measuring device.

10. The method of claim 9 wherein the storage of x axis values, y axis values and distance values is in the electronic memory of a computer.

11. The method of claim 10 wherein the biological surface is a wound bed or a dermal surface.

12. The method of claim 10 wherein the biological surface is vascular tissue including heart valves, veins and arteries.

13. The method of claim 10 wherein the relative height value has a uncertainty of less than 0.1 inches (0.25 cm).

14. A method of determining the dimensional characteristics of a biological object, the method comprising:

measuring without physical contact or disruption of sterility the length, width and height above or below a reference plane of the biological object with an optical distance measuring device thereby creating a data set;

processing the data set in a computer so as to determine the dimensional characteristics of the biological feature.

15. The method of claim 14 wherein the optical distance measuring means is a laser based distance measuring device.

16. The method of claim 9 wherein the data set is comprised of x axis values, y axis values and distance values relative to a predetermined reference plane and said data set is stored in the electronic memory of a computer.

17. The method of claim 14 wherein the biological object is a wound bed or a dermal surface.

18. The method of claim 14 wherein the biological object is vascular tissue including heart valves, veins and arteries.

* * * * *